US008226959B2

(12) United States Patent
Gibson et al.

(10) Patent No.: US 8,226,959 B2
(45) Date of Patent: Jul. 24, 2012

(54) VACCINE COMPOSITIONS

(75) Inventors: Peter Gibson, Merewether (AU); Philip Hansbro, The Hill (AU)

(73) Assignee: Newcastle Innovation Pty Ltd, Callaghan, New South Wales (AU)

( * ) Notice: Subject to any disclaimer, the term of this patent is extended or adjusted under 35 U.S.C. 154(b) by 0 days.

(21) Appl. No.: 12/865,507

(22) PCT Filed: Feb. 2, 2009

(86) PCT No.: PCT/AU2009/000120
§ 371 (c)(1),
(2), (4) Date: Dec. 23, 2010

(87) PCT Pub. No.: WO2009/094730
PCT Pub. Date: Aug. 6, 2009

(65) Prior Publication Data
US 2011/0091506 A1    Apr. 21, 2011

(30) Foreign Application Priority Data

Feb. 1, 2008    (AU) ................................. 2008900449

(51) Int. Cl.
*A61K 39/09*    (2006.01)
(52) U.S. Cl. ............... 424/244.1; 424/236.1; 424/193.1; 424/197.11; 536/123.1
(58) Field of Classification Search ......................... None
See application file for complete search history.

(56) References Cited

U.S. PATENT DOCUMENTS

| 5,565,204 A | 10/1996 | Kuo et al. |
| 2005/0031646 A1 | 2/2005 | Capiau et al. |

FOREIGN PATENT DOCUMENTS

| WO | 2004043376 | 5/2004 |
| WO | 2004089407 | 10/2004 |
| WO | 2006032499 | 3/2006 |
| WO | 2007071707 | 6/2007 |

OTHER PUBLICATIONS

International Search Report and Written Opinion for Application No. PCT/AU2009/000120 dated Mar. 16, 2009 (10 pages).
Berry, L.J. et al., "Transcutaneous Immunization with Combined Cholera Toxin and CpG Adjuvant Protects Against *Chlamydia muridarum* Genital Tract Infection," Infect & Immunity (2004) 72:2:1019-1028.
Carlsen, K.H., "Therapeutic Strategies for Allergic Airways Diseases," Paediatric Respiratory Reviews (2004) 5:45-51.
Foster, P.S. et al., "Interleukin 5 Deficiency Abolishes Eosinophilia, Airways Hyperreactivity, and Lung Damage in a Mouse Asthma Model," J. Exp. Med. (1996) 183:195-201.
Jones, P.D. et al., "The Prevalence of Asthma Appears to be Inversely Related to the Incidence of Typhoid and Tuberculosis: Hypothesis to Explain the Variation in Asthma Prevalence Around the World," Med. Hypotheses (2000) 55:1:40-42.
Michon, F. et al., "Multivalent Pneumococcal Capsular Polysaccharide Conjugate Vaccines Employing Genetically Detoxified Pneumolysin as a Carrier Protein," Vaccine (1998) 16:18:1732-41.
Preston, J.A. et al., "Inhibition of Allergic Airways Disease by Immunomodulatory Therapy with Whole Killed *Streptococcus pneumoniae*," Vaccine (2007) 25:8154-8162.
Takeda, K et al. "Development of Eosinophilic Airway Inflammation and Airway Hyperresponsiveness in Mast Cell-Deficient Mice," J. Exp. Med. (1997) 186:3:449-454.
Talbot, T.R. et al., "Asthma as a Risk Factor for Invasive Pneumococcal Disease," N. Engl. J. Med. (2005) 352:2082-2090.
Tuomanen, E. et al., "The Relative Role of Bacterial Cell Wall and Capsule in the Induction of Inflammation in Pneumococcal Meningitis," J. Infect. Dis. (1985) 151:3:535-540.

*Primary Examiner* — Jennifer Graser
(74) *Attorney, Agent, or Firm* — Michael Best & Friedrich LLP

(57) ABSTRACT

The present invention provides methods for the treatment or prevention of allergic airways diseases, the suppression of allergic immune responses, and the induction protective immunity against allergic airways diseases wherein the methods comprise administering to subjects in need thereof an effective amount of a *Streptococcus pneumoniae* capsular polysaccharide and a *Streptococcus pneumoniae* exotoxin or exotoxoid, optionally together with one or more additional antigenic or immunomodulatory constituents, components or fractions of *Streptococcus pneumoniae* and/or immunopotentiators. Administration of individual components is also contemplated. Also provided are vaccine compositions suitable for use in accordance with methods disclosed herein.

11 Claims, 14 Drawing Sheets

VACCINE COMPOSITIONS

CROSS-REFERENCE TO RELATED APPLICATIONS

This patent application is a national stage filing under 35 U.S.C. 371 of International Application No. PCT/AU2009/000120, filed on Feb. 2, 2009, which claims foreign priority benefits to Australian Patent Application No. 2008900449, filed on Feb. 1, 2008. These applications are incorporated herein by reference in their entireties.

FIELD OF THE INVENTION

The present invention relates generally to methods for the treatment and prevention of allergic airways diseases such as asthma. More particularly the invention relates to the immunization of individuals using vaccines and/or therapies based on constituents of *Streptococcus pneumoniae* and to the use of such vaccines and/or therapies for the treatment or prevention of allergic airways diseases.

BACKGROUND OF THE INVENTION

Allergic airways diseases such as asthma and allergic rhinitis are of major, and increasing, public health concern, especially in industrialised nations where they represent the most common chronic disorders in children. Asthma, in particular, is a chronic respiratory disorder that has increased alarmingly in prevalence in the last 20 years. Australia has one of the highest rates of asthma in the world, with estimates suggesting that up to 10-20% of the population are affected. Worldwide up to one in four children, one in seven adolescents and one in ten adults will experience symptoms of asthma at some time in their life. In addition to being potentially debilitating for sufferers, the direct and indirect costs of allergic airways diseases on health systems are substantial. In the United States it has been estimated that the direct cost of asthma to the economy is in the order of $15 billion annually, with direct medication costs accounting for about $3 billion of this.

There is a clear need not only for effective therapies for the treatment and management of allergic airways diseases, but also for strategies and approaches to prevent the onset and development of such diseases.

Asthma is an inflammatory disorder causing variability of airflow obstruction, and an increased sensitivity and exaggerated response to many different stimuli (airway hyperresponsiveness), particularly allergens. Together these patho-physiological manifestations lead to symptoms including wheezing, coughing, chest tightness and dyspnoea. The chronic inflammatory response in asthma is characterised by an intense eosinophil infiltrate into the airways and mucous secreting cell hyperplasia that is coordinated by cytokine release from T-helper type 2 (Th2) lymphocytes. Eosinophils release a range of both preformed and newly synthesised mediators that damage the mucosal epithelial lining and promote an exaggerated repair response resulting in tissue remodeling and sub-epithelial fibrosis.

It has been noted that the prevalence of asthma varies inversely with the prevalence of certain bacterial infections such as tuberculosis and typhoid (see for example Jones et al., 2000). These infections, together with those of *Mycobacterium Bovis* elicit a T-helper type 1 (Th1) immune response, which, during the early years of life, may cause immune deviation from the neonatal Th2 response to a mature Th1 response. The absence of exposure to Th1 inducing infections is thought to promote the persistence of a Th2 phenotype and permits the development of allergy and asthma.

The increasing prevalence of allergic airways diseases, and the increasingly early onset of diseases such as asthma in children, has focused much attention on the need for effective treatments and preventative measures. Whilst research continues, to date there has yet to emerge any effective means of preventing the onset or development of allergic airways diseases such as asthma.

SUMMARY OF THE INVENTION

According to a first aspect of the present invention there is provided a method for the treatment or prevention of an allergic airways disease in a subject, the method comprising administering to the subject an effective amount of a *Streptococcus pneumoniae* capsular polysaccharide and a *Streptococcus pneumoniae* exotoxin or exotoxoid.

In an embodiment the capsular polysaccharide is the type 3 polysaccharide (T3P) or a precursor, derivative or variant thereof.

In an embodiment the exotoxin is pneumolysin or a precursor, derivative or variant thereof. The pneumolysin may be in the form of pneumolysoid (Ply).

The method may further comprise the administration of one or more additional antigenic or immunomodulatory constituents, components or fractions of *Streptococcus pneumoniae*. Exemplary constituents, components and fractions include purified cell walls, cell wall peptidoglycan, lipoteichoic acid, polysaccharides, proteins (intracellular or extracellular such as pneumococcal surface adhesion, surface protein or a choline binding protein), lipids, carbohydrates, glycoproteins, and fragments thereof. In one embodiment the additional constituent, component or fraction is purified *Streptococcus pneumoniae* cell wall. The purified cell wall may be derived from an encapsulated or unencapsulated strain.

In an embodiment, the method comprises the administration of a *Streptococcus pneumoniae* capsular polysaccharide, a *Streptococcus pneumoniae* exotoxin or exotoxoid and purified cell wall, optionally from an unencapsulated *Streptococcus pneumoniae* strain. In a particular embodiment the capsular polysaccharide is T3P and the exotoxoid is Ply.

The method may further comprise the administration of an immunopotentiator. The immunopotentiator may comprise CpG oligonucleotides.

In an embodiment, the method comprises the administration of a *Streptococcus pneumoniae* capsular polysaccharide, a *Streptococcus pneumoniae* exotoxin or exotoxoid and CpG oligonucleotides. In a particular embodiment the capsular polysaccharide is T3P and the exotoxoid is Ply.

In an embodiment, the method comprises the administration of a *Streptococcus pneumoniae* capsular polysaccharide, a *Streptococcus pneumoniae* exotoxin or exotoxoid, CpG oligonucleotides and purified cell wall, optionally from an unencapsulated *Streptococcus pneumoniae* strain. In a particular embodiment the capsular polysaccharide is T3P and the exotoxoid is Ply.

Typically the capsular polysaccharide and exotoxin or exotoxoid, and optionally additional molecules/constituents, are administered as a composition. The composition may be in the form of a vaccine and the administration may comprise vaccination. The vaccine may be a therapeutic or prophylactic vaccine.

The allergic airways disease may be selected from asthma, asthma exacerbations, eosinophilic bronchitis, allergic rhinitis, chronic cough, sinusitis, angioedema, urticaria, chronic obstructive pulmonary disease, conjunctivitis and hay fever. The asthma may be chronic or acute.

The treatment or prevention may prevent or suppress the onset of an allergic airways disease.

In an embodiment, administration is selected from intratracheal, intranasal, intramuscular, subcutaneous and transcutaneous.

According to a second aspect of the present invention there is provided a vaccine composition for use in the treatment or prevention of allergic airways diseases, eosinophilia, mucous secreting cell expression, airway hyperresponsiveness or Th2-mediated disease, the vaccine composition comprising a *Streptococcus pneumoniae* capsular polysaccharide and a *Streptococcus pneumoniae* exotoxin or exotoxoid.

In an embodiment the capsular polysaccharide is the type 3 polysaccharide (T3P) or a precursor, derivative or variant thereof.

In an embodiment the exotoxin is pneumolysin or a precursor, derivative or variant thereof. The pneumolysin may be in the form of pneumolysoid (Ply).

The vaccine composition may further comprise one or more additional antigenic or immunomodulatory constituents, components or fractions of *Streptococcus pneumoniae*. Exemplary constituents, components and fractions include purified cell walls, cell wall peptidoglycan, lipoteichoic acid, polysaccharides, proteins (intracellular or extracellular such as pneumococcal surface adhesion, surface protein or a choline binding protein), lipids, carbohydrates, glycoproteins, and fragments thereof. In one embodiment the additional constituent, component or fraction is purified *Streptococcus pneumoniae* cell wall. The purified cell wall may be derived from an encapsulated or unencapsulated strain.

The vaccine composition may further comprise an immunopotentiator. The immunopotentiator may comprise CpG oligonucleotides.

In one embodiment, the vaccine composition comprises T3P, Ply, purified cell wall from an unencapsulated *Streptococcus pneumoniae* strain and CpG oligonucleotides.

The allergic airways disease may be selected from asthma, asthma exacerbations, eosinophilic bronchitis, allergic rhinitis, chronic cough, sinusitis, angioedema, urticaria, chronic obstructive pulmonary disease, conjunctivitis and hay fever.

According to a third aspect of the present invention there is provided a method for inducing protective immunity against an allergic airways disease in a subject, the method comprising administering to the subject an effective amount of a *Streptococcus pneumoniae* capsular polysaccharide and a *Streptococcus pneumoniae* exotoxin or exotoxoid.

According to a fourth aspect of the present invention there is provided a method for the suppression of an allergic immune response in a subject, the method comprising administering to the subject an effective amount of a *Streptococcus pneumoniae* capsular polysaccharide and a *Streptococcus pneumoniae* exotoxin or exotoxoid.

The allergic immune response may be associated with, for example, eosinophilia, mucous secreting cell expression, airway hyperresponsiveness and/or any Th2-mediated immune response. The eosinophilia may be peripheral or tissue eosinophilia.

According to a fifth aspect of the present invention there is provided a method for the treatment or prevention of one or more of eosinophilia, mucous secreting cell expression, airway hyperresponsiveness and/or Th2-mediated disease in a subject, the method comprising administering to the subject an effective amount of a *Streptococcus pneumoniae* capsular polysaccharide and a *Streptococcus pneumoniae* exotoxin or exotoxoid.

The eosinophilia may be peripheral or tissue eosinophilia.

According to a sixth aspect of the invention there is provided a method for the treatment or prevention of an allergic airways disease in a subject, the method comprising administering to the subject an effective amount of a *Streptococcus pneumoniae* capsular polysaccharide and a *Streptococcus pneumoniae* exotoxin, optionally together with purified *Streptococcus pneumoniae* cell wall and/or CpG oligonucleotides.

According to a seventh aspect of the invention there is provided a vaccine composition for use in the treatment or prevention of allergic airways diseases, eosinophilia, mucous secreting cell expression, airway hyperresponsiveness or Th2-mediated disease, the vaccine composition comprising a *Streptococcus pneumoniae* capsular polysaccharide and a *Streptococcus pneumoniae* exotoxin or exotoxoid, optionally together with purified *Streptococcus pneumoniae* cell wall and/or CpG oligonucleotides.

According to an eighth aspect of the invention there is provided the use of a *Streptococcus pneumoniae* capsular polysaccharide and a *Streptococcus pneumoniae* exotoxin or exotoxoid for the manufacture of a vaccine composition for the treatment or prevention of allergic airways diseases.

In further aspects of the invention, also provided herein are methods for the treatment or prevention of allergic airways diseases, for inducing protective immunity against an allergic airways disease, and for suppressing an allergic immune response, the methods comprising the administration of an effective amount of one or more of a *Streptococcus pneumoniae* capsular polysaccharide, a *Streptococcus pneumoniae* exotoxin or exotoxoid, CpG oligonucleotides and purified cell wall, optionally from an unencapsulated *Streptococcus pneumoniae* strain. Vaccine compositions comprising purified one or more of a *Streptococcus pneumoniae* capsular polysaccharide, a *Streptococcus pneumoniae* exotoxin or exotoxoid, CpG oligonucleotides and purified cell wall, optionally from an unencapsulated *Streptococcus pneumoniae* strain, and uses thereof are also provided.

Aspects and embodiments of the present invention are applicable to any organism susceptible to allergic airways diseases. Typically the subject is a mammal. Typically the mammal is a human.

BRIEF DESCRIPTION OF THE DRAWINGS

Embodiments of the present invention will now be described, by way of example only, with reference to the accompanying drawings.

DETAILED DESCRIPTION OF THE INVENTION

Figure 1:
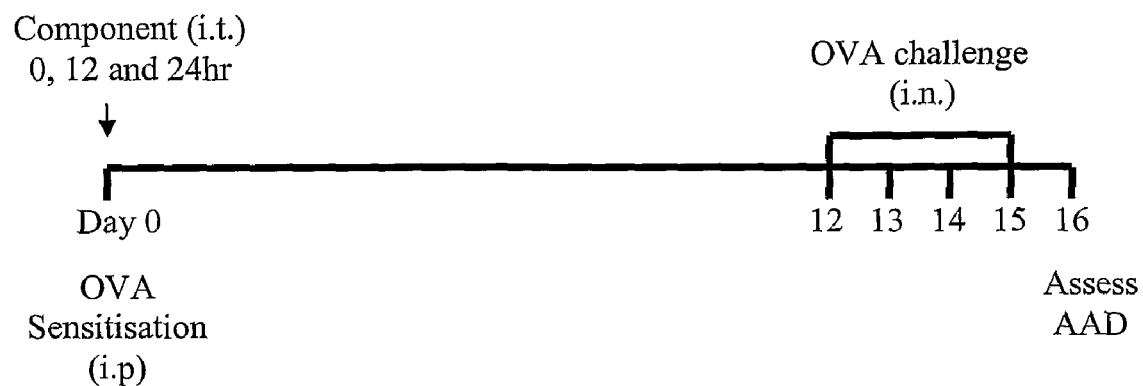
FIG. 1. Schematic representation of the experimental protocol described herein for evaluating the effect of *Streptococcus pneumoniae* constituents, and combinations thereof, on allergic airways disease in a mouse model.

The articles "a" and "an" are used herein to refer to one or to more than one (i.e., to at least one) of the grammatical object of the article. By way of example, "an element" means one element or more than one element.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

As used herein the term "treatment", refers to any and all uses which remedy a disease state or one or more symptoms thereof, or otherwise prevent, hinder, retard, or reverse the progression of disease or other undesirable symptoms in any way whatsoever.

As used herein the term "prevention" means generally the prevention of the establishment of an allergic airways disease. In accordance with accepted classification and nomenclature, prevention may be primary, secondary or tertiary (see for example, Carlsen, 2004). Primary prevention refers to the prevention of the establishment of the disease. In one context, this may refer to strategies and approaches adopted at a community level in order to reduce the incidence of the disease, or to an individual level wherein the individual may have no indications of susceptibility to the diseases or of being 'high risk'. Secondary prevention refers to intervention in individuals who are at high risk for the development of the allergic airways disease and who have not yet developed the disease, but may or may not have exhibited some allergic symptoms. These individuals may have a family history of allergic disease and/or one or more of atopic dermatitis or eczema, food allergy, bronchial hyperreactivity, blood eosinophilia, airway eosinophilia, mucous secreting cell expression, Th2-mediated disease, elevated total IgE levels, elevated allergen-specific IgE, or skin-test reactivity to specific allergens. Tertiary prevention refers to preventing the worsening of the disease and reducing the symptoms experienced by allergic patients.

As used herein the term "effective amount" refers to the ability of a molecule, agent, cell constituent or combination of molecules, agents and cell constituents to induce an immune response suitable and sufficient to have the desired effect, for example, the treatment or prevention of an allergic airways disease, protection of a subject against an allergic airways disease, and/or the treatment or prevention of eosinophilia, mucous secreting cell expression, airway hyperresponsiveness and/or Th2-mediated disease. The vaccination or therapy carried out in accordance with the invention typically results in the inducement of an innate and an adaptive immune response. Accordingly, typically the "effective amount" is an "immunologically effective amount" such that the amount is sufficient to induce both an innate and an adaptive immune response.

The terms "vaccination" and "vaccinating" mean the inoculation of a substance or composition (a vaccine) into the body of the subject for the purpose of producing immunity against a disease, that is for the purpose of treating or preventing a disease. Accordingly, vaccination may be therapeutic or prophylactic. By therapeutic vaccination is meant the administration of a vaccine to an individual already suffering from an allergic airways disease, typically for the purpose of heightening or broadening the immune response to thereby halt, impede or reverse the progression of the disease. The terms "vaccination" and "immunization" are used interchangeably herein. Similarly, the terms "vaccination" and "administration" are used interchangeably herein in certain contexts.

The term "derivative" includes functional fragments, parts, portions or variants of a molecule or compound, from either natural or non-natural sources. Non-natural sources include, for example, recombinant or synthetic sources. By "recombinant sources" is meant that the cellular source from which the subject molecule is harvested has been genetically altered. This may occur, for example, in order to increase or otherwise enhance the rate and volume of production by that particular cellular source. Parts or fragments include, for example, functionally active regions of the molecule or compound that may be produced by synthetic or recombinant means well known to those skilled in the art. In the case of proteins and polypeptides, derivatives may also be derived from insertion, deletion or substitution of amino acids. Protein and polypeptide derivatives also include fragments having particular parts of the protein fused to peptides, polypeptides or other proteinaceous or non-proteinaceous molecules.

As used herein the term "variant" means a molecule or compound which exhibits at least some of the functional activity of the molecule or compound of which it is a variant. A variant may take any form and may be naturally or non-naturally occurring.

The term "antigen" as used herein refers to any substance or product or mixture of substances or products capable of eliciting an immune response (also referred to herein as immunomodulatory agents). Accordingly, an antigen may comprise crude fractions, lysates, purified or partially purified cellular components or constituents or mixtures or combinations of any of the above.

As used herein the term "oligonucleotide" refers to a single-stranded sequence of deoxyribonucleotide or ribonucleotide bases, known analogues of natural nucleotides, or mixtures thereof. Oligonucleotides are typically short (for example less than 50 nucleotides in length) sequences which may be prepared by any suitable method, including, for example, direct chemical synthesis or cloning and restriction of appropriate sequences.

*Streptococcus pneumoniae*, a common respiratory pathogen, is the predominant cause of community-acquired pneumonia in children and adults, and frequently induces otitis media, septicaemia and meningitis. *Streptococcus pneumoniae* vaccination has been recommended to prevent invasive *Streptococcus pneumoniae* disease in "high risk" groups, including asthmatics (Salisbury and Begg, 1996) and asthma has been suggested as an independent risk factor for invasive *Streptococcus pneumoniae* disease (Talbot et al., 2005). However *Streptococcus pneumoniae* infection is not widely implicated in the development and exacerbation of asthma.

As disclosed in co-pending International Patent Application No. PCT/AU2007/001098, the disclosure of which is incorporated herein in its entirety, using a mouse model of Th2-driven allergic airways diseases, the present inventors have demonstrated that not only does *Streptococcus pneumoniae* infection have a protective effect against development of allergic airways diseases, but surprisingly immunization using whole killed bacteria also suppresses the hallmark features of allergic airways diseases. These include inhibition of type 2 cytokine and antibody responses, inhibition of peripheral and tissue eosinophilia, inhibition of goblet cell hyperplasia and inhibition of airways hyperresponsiveness. In particular, eosinophilia is linked to the ongoing remodeling of the airways in diseases such as chronic asthma. Without wishing to be bound by theory, as both innate and adaptive immune responses are important in the clearance of, and protection against, *Streptococcus pneumoniae* infection, either or both the innate and adaptive immune systems may be involved in inhibiting the development and progression of allergic airways diseases such as asthma upon *Streptococcus pneumoniae* vaccination or therapy in accordance with the invention.

As described herein, the inventors have now identified particular combinations of *Streptococcus pneumoniae* constituents that are capable of mimicking the protective effect of *Streptococcus pneumoniae* infection and which exhibit advantageous properties as therapeutic and prophylactic vaccine compositions. As exemplified herein a combination of the capsular type 3 polysaccharide T3P and pneumolysoid (Ply), the non-toxic form of the pneumolysin protein, successfully reduces the hallmark features of allergic airways diseases, as determined for example by a reduction in BALF eosinophilia, a reduction in airways hyperresponsiveness and reductions in the levels of IL-5 and IL-13. Significantly, the combination of T3P and Ply are more effective than whole killed *Streptococcus pneumoniae*, the administration of which results in an adverse IFNγ response. Further, purified cell wall from an unencapsulated *Streptococcus pneumoniae* strain is also shown herein to reduce BALF eosinophil levels, lymph node IL-13 levels and the levels of IL-5 and IL-13 from spleen lymphocytes. Moreover, BALF eosinophils, Th2 cytokines and airways hyperresponsiveness are shown to be significantly reduced following the administration of a combination of Ply, T3P and purified cell wall, a combination of Ply, T3P and CpG olignucleotides, and a combination of Ply, T3P, purified cell wall and CpG olignucleotides.

Thus, the findings disclosed herein open up novel and powerful avenues for the treatment and prevention of allergic airways diseases such as asthma based on immunization or therapy using constituents or components of *Streptococcus pneumoniae* capable of inducing an immune response.

Accordingly, one aspect of the present invention relates to a method for the treatment or prevention of allergic airways disease in a subject, the method comprising administering to the subject an effective amount of a *Streptococcus pneumoniae* capsular polysaccharide and a *Streptococcus pneumoniae* exotoxin.

In a particular embodiment the capsular polysaccharide is the type 3 polysaccharide (T3P) or a precursor, derivative or variant thereof. In a particular embodiment the exotoxin is pneumolysin or a precursor, derivative or variant thereof. In a particular embodiment the pneumolysin may be in the form of pneumolysoid (Ply). Pneumolysin/pneumolysoid is one of the most immunogenic proteins of *Streptococcus pneumoniae* and is critical in protection and in stimulating a strong T cell response and T cell chemotaxis. Ply also induces immune responses through the activation of MyD88 and the toll-like receptors TLR-2 and TLR-4. The T3P capsular polysaccharide is implicated in the induction of an adaptive immune response via, for example, the induction of antibody responses and through toll-like receptors. Hereinafter, the term "exotoxin" is used to encompass both an exotoxin and equivalent or corresponding extoxoid.

The capsular polysaccharide and the exotoxin are typically derived from *Streptococcus pneumoniae*. By "derived" is meant that the polysaccharide and exotoxin are equivalent to those found in *Streptococcus pneumoniae*. The polysaccharide and exotoxin may be derived from *Streptococcus pneumoniae* in that they are purified or isolated from *Streptococcus pneumoniae*, or alternatively they may be synthetically or recombinantly produced. Also encompassed by the present invention are precursors, derivatives and variants of the capsular polysaccharide and exotoxin. Such precursors, derivatives and variants may also be purified or isolated from *Streptococcus pneumoniae*, or may be synthetically or recombinantly produced.

The capsular polysaccharide and the exotoxin may be conjugated to enhance immunogenicity. As exemplified in U.S. Pat. No. 5,565,204 (Kuo et al.), the disclosure of which is incorporated herein in its entirety, an immunogenic capsular polysaccharide may be conjugated with the pneumolysin protein or fragment thereof. Thus, in accordance with an embodiment of the present invention the T3P and Ply may be conjugated. Conjugation may be achieved by any suitable means, such means being known to those skilled in the art.

Embodiments of the present invention also contemplate the administration of one or more *Streptococcus pneumoniae* antigenic or immunomodulatory fractions, components or constituents in addition to the capsular polysaccharide and exotoxin. A suitable antigenic or immunomodulatory fraction may be, for example, purified *Streptococcus pneumoniae* cell walls or an extract of whole bacteria produced by any suitable means such as lysis or sonication. Purified cell wall fractions may be derived from encapsulated or unencapsulated strains. Suitable antigenic or immunomodulatory components or constituents may comprise intracellular, extracellular (such as a secreted protein or polypeptide), capsule-associated, cell wall-associated or cell membrane-associated components or cellular constituents and thus may be protein, polypeptide, peptide, polysaccharide, carbohydrate, lipid, lipopolysaccharide, or glycoprotein. The protein, polypeptide or peptide may comprise, for example, pneumococcal surface adhesin (PsaA), *Streptococcus pneumoniae* surface protein (PspA) or a choline binding protein (such as CbpA). An antigenic or immunomodulatory component or constituent may comprise any two or more of the aforementioned constituents. An antigenic component may be an epitope, for example a peptide sequence, polysaccharide or carbohydrate epitope, or the like, derived from a *Streptococcus pneumoniae* cellular constituent. The antigen may be natural or modified from its native state, or may be synthetically produced. An antigen suitable for use in accordance with the invention may generate either an adaptive immune response or innate immune response, or both. The immune response may be produced directly by the antigen or indirectly, such as via the inhibition or activation of one or more host factors. For example, the antigen may induce the required immune response via activation of one or more of MyD88, TLR-2 and TLR-4.

In accordance with embodiments of the invention constituents may be administered individually (such that individual constituents may be administered via different routes, at different doses and/or at different times) or together, for example in the form of a single composition. The composition may be in the form of a vaccine, and thus the administration of the subject may comprise vaccination of the subject with a vaccine.

Accordingly, an aspect of the invention provides a vaccine composition for use in the treatment or prevention of allergic airways diseases, eosinophilia, mucous secreting cell expression, airway hyperresponsiveness or Th2-mediated disease, the vaccine composition comprising a *Streptococcus pneumoniae* capsular polysaccharide and a *Streptococcus pneumoniae* exotoxin.

Vaccine compositions in accordance with the invention may further comprise one or more *Streptococcus pneumoniae* antigenic or immunomodulatory fractions, components or constituents in addition to the capsular polysaccharide and exotoxin, as described hereinbefore.

The efficacy of methods and vaccine compositions in accordance with the invention may be enhanced by the use of one or more adjuvants (immunopotentiators). Such adjuvants or immunopotentiators enhance, accelerate, prolong or otherwise potentiate the immune response elicited by the vaccine composition. Suitable adjuvants are known to those skilled in the art and may be synthetic or natural and exogenous or endogenous to the subject to be treated. Suitable immunopotentiators capable of enhancing the delivery or protective or therapeutic efficacy of bacterial vaccines (for example by boosting the immune response produced) are known to those skilled in the art. For example, the incorporation of bacterial DNA in the form of CpG oligodeoxynucleotides (CpG oligonulceotides) are able to act as strong adjuvants for bacterial vaccines and stimulate Th1 type immune responses (Berry et al., 2004). As will be appreciated by those skilled in the art, suitable CpG oligonucleotides may be of any suitable lengh and specific sequence provided they contain one or more CG dinucleotide pairs.

Other suitable immunopotentiators include, but are not limited to, mineral salts (such as aluminium hydroxide), oil emulsions and surfactant based formulations, virosomes, biodegradable cationic polylactide-co-glycolide (PLG) microparticles, microbial derivatives including lipids (such as monophosphoryl lipid A), mono- and polysaccharides, and modified toxins such as cholera toxin and heat labile enterotoxin, inert particles such as gold particles, and endogenous human adjuvants such as GM-CSF and IL-12. Two or more adjuvants or immunopotentiators may be used in combination.

Particular embodiments of the methods and vaccines of the invention provide for the administration of a *Streptococcus pneumoniae* capsular polysaccharide, a *Streptococcus pneumoniae* exotoxin and one or more of purified *Streptococcus pneumoniae* cell walls and CpG oligonucleotides.

Any of these constituents may be conjugated to any other, or a suitable carrier molecule or compound to enhance immunogenicity. Conjugation can be by any suitable means, which means are known to those skilled in the art.

Particular embodiments of the methods and vaccines of the invention also provide for the administration of any one or more of a *Streptococcus pneumoniae* capsular polysaccharide, a *Streptococcus pneumoniae* exotoxin and one or more of purified *Streptococcus pneumoniae* cell walls and CpG oligonucleotides.

Embodiments of the present invention find application in the treatment and prevention of a range of allergic airways diseases, including but not limited to asthma, asthma exacerbations, eosinophilic bronchitis, allergic rhinitis, chronic cough, sinusitis, angioedema, urticaria, chronic obstructive pulmonary disease, conjunctivitis and hay fever. In particular, the present invention may be employed in the treatment or prevention of allergic airways diseases associated with a Th2 immune response and the suppression of allergic immune responses.

Further, administration in accordance with embodiments of the invention may suppress IgE responses in the subject, which IgE responses are characteristic of allergic airways diseases. Allergic immune responses capable of being suppressed by administration in accordance with embodiments of the invention may be characterized by, for example, one or more of IgE responses, elevated release of Th1 and/or Th2 cytokines (such as IFNγ, IL-5 and IL-13) by, for example, T cells and mast cells, and eosinophilia.

Vaccination in accordance with the invention may provide protective immunity against allergic airways diseases to the subject being vaccinated. That is, the component(s) of the vaccine may elicit a protective immune response in the subject, for example by inducing the production of antibodies, innate immunity or adaptive immunity against the component(s). As used herein, the term "protective immunity" refers to the ability of a molecule or composition administered to a subject to elicit an appropriate immune response in the subject and thereby provide protection to the subject from the development or progression of an allergic airways disease.

Inoculation of a subject with a composition or vaccine in accordance with the invention sufficient to produce the desired therapeutic or prophylactic effect may require only a single administration (or vaccination). In another embodiment of the present invention, the administration regime may comprise a series of administrations to produce a full, broad immune response. For example, when multiple administrations or vaccinations are required, the vaccinations can be provided at suitable intervals depending on the circumstances and the desired outcome; the interval may be hours, days, months or years. For example the interval between administrations or vaccinations may be from about 24 hours to about 6 months; about 24 hours, about 48 hours, about 72 hours, about one week, about two weeks, about one month, about 3 months or about 6 months or longer. Alternatively, it may be appropriate to space administrations or vaccinations over a period of years, such as for example about 1 year, about 2 years, about 3 years, about 4 years, about 5 years, about 10 years or longer. When multiple administrations or vaccinations are required, the doses may or may not be equal doses and similarly when more than two administrations or vaccinations are required the time intervals between individual administrations or vaccinations may or may not be the same. The optimal quantity and spacing of individual dosages will be determined by a variety of factors including the particular disease to be treated or prevented, the form, route and site of administration, and the particular individual being treated. Such optimum conditions can be determined by conventional techniques well known to those skilled in the art.

The effective dose level for any particular patient will depend upon a variety of factors including: the disease to be treated or prevented (and in the case of therapeutic treatment, the severity of the disease), the particular vaccine employed; the age, body weight, general health, sex and diet of the patient; the time of administration; the route of administration; the rate of sequestration of the agent or compound; the duration of the treatment; drugs used in combination or coincidental with the treatment, together with other related factors well known in medicine.

Those skilled in the art will also readily appreciate that as used herein the terms "effective amount" and "effective dose" include within their meaning a non-toxic but sufficient amount of an agent or compound to provide the desired therapeutic or prophylactic effect. The exact amount required will vary from subject to subject. Thus, it is not possible to specify an exact "effective amount". One skilled in the art would be able, by routine experimentation, to determine an effective, non-toxic amount of a composition or vaccine which would be required to treat applicable diseases.

By way of example only, an effective dosage may be in the range of about 0.0001 mg to about 1000 mg per kg body weight; about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. Individual dosages of vaccine may comprise about 0.1 to about 5000 µg active component(s), typically about 1 to about 500 µg, about 10 to about 250 µg, about 10 to about 250 µg, about 20 to about 200 µg, about 25 to 100 µg or about 25 to about 50 µg of active components(s).

Routes of administration suitable for methods of the present invention include, but are not limited to, oral (including by inhalation, ingestion or sublingual administration), nasal, topical, parenteral (intratracheal, intramuscular, subcutaneous, intravenous, intraarterial), transmucosal, transcutaneous and transdermal. Administration may be local, regional or systemic.

In general, suitable compositions may be prepared according to methods that are known to those of ordinary skill in the art and accordingly may include a pharmaceutically acceptable carrier, diluent and/or adjuvant. For administration in accordance with the present invention, a suitable vaccine may be formulated in a pharmaceutically acceptable carrier according to the mode and route of administration to be used. The carriers, diluents and adjuvants must be "acceptable" in terms of being compatible with the other ingredients of the composition, and not deleterious to the recipient thereof. Typically a sterile water or isotonic formulation is employed. For example, a suitable isotonic solution is phosphate buffered saline or Ringer's solution.

Other examples of pharmaceutically acceptable carriers or diluents are vegetable based oils such as peanut oil, safflower oil, olive oil, cottonseed oil, maize oil, sesame oils arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration. Typically, the carrier or carriers will form from 10% to 99.9% by weight of the compositions.

Formulations may further comprise suitable adjuvants. Adjuvants typically include emollients, emulsifiers, thickening agents, preservatives, bactericides and buffering agents.

For administration as an injectable solution or suspension, non-toxic parenterally acceptable diluents or carriers can include, Ringer's solution, isotonic saline, phosphate buffered saline, ethanol and 1,2 propylene glycol.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof. Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Compositions may be administered in the form of liposomes. Liposomes are generally derived from phospholipids or other lipid substances, and are formed by mono- or multilamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 of seq., the contents of which are incorporated herein by reference.

Those skilled in the art will appreciate that the methods and vaccinations contemplated by the present invention may be carried out in conjunction with other therapies or preventative measures for the treatment or prevention of allergic airways diseases or symptoms associated with such diseases. For example, immunotherapy based on sensitisation and challenge with allergens is typically used in the treatment or prevention of asthma. Further, the administration of agonists of various cellular receptors such as TLR-2 and TLR-4 may also be employed. For such Combination therapies, each component of the combination therapy may be administered at the same time, or sequentially in any order, or at different times, so as to provide the desired effect. Alternatively, the components may be formulated together in a single dosage unit as a combination product. For example, *Streptococcus pneumoniae* components or constituents thereof can be combined with immunizing or other non-immunizing components to produce a multivalent vaccine or with other medicaments. When administered separately, components may be administered by the same route of administration, although it is not necessary for this to be so.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

Example 1

Mouse Model of Th2-Induced Allergic Airways Diseases

The present inventors have established an experimental model of allergic airways disease in BALB/c mice (Th2 and IgE responding), based on sensitization consistency and subsequent challenge with ovalbumin (OVA). This model is described in co-pending International PCT Application No. PCT/AU2007/001098, the disclosure of which is incorporated herein in its entirety.

Briefly, female BALB/c mice (6-8 week old) were obtained from the Central Animal House, University of Newcastle. For the induction of allergic airways disease, mice were sensitized by intraperitoneal injection of OVA (50 ug; Sigma, Missouri, USA) at day 0 using OVA in Rehydrogel (1 mg, Reheis, Berkeley Heights, USA) in sterile saline (200 µl) and mice were subsequently challenged by intranasal droplet application of OVA (day 12-15; 10 ug, 50 ul sterile saline).

For the experiments described in the subsequent examples, whole killed *Streptococcus pneumoniae* or components derived therefrom were administered to the mice intratracheally in three doses, every 12 hours beginning at the time of OVA sensitization on day 0. The protocol employed is illustrated in FIG. 1. OVA challenge on days 12-15 is followed by assessment of allergic airways disease features on day 16. In the experimental model (absent vaccine administration), on day 16 mice show the hallmark features of allergic airways disease, including increased BALF and blood eosinophils, increased T helper 2 (Th2) cell cytokines and airways hyperresponsiveness.

Airways hyperresponsiveness was assessed at day 16 in live animals. Mice were sacrificed by intraperitoneal injection of sodium pentobarbitone (2000) for the assessment of inflammatory responses. Control mice received saline sensitisation and OVA challenge. Mice were held in specific pathogen free conditions, and all procedures were approved by the University of Newcastle Animal Care and Ethics Committee.

Inflammatory responses and airways hyerresponsiveness were assessed in accordance with the following procedures.

In measuring mediastinal lymph node T cell cytokine production, mediastinal lymph nodes were isolated, homogenised and cultured at $10^6$ cells/well (96 h, 37° C., 5% $CO_2$), before stimulation as described in Berry et al., 2004 using 200 ug/ml OVA as the stimulant. Cell-free culture supernatants were stored at −20° C. IL-5, IL-13 and IFNγ concentrations were determined by ELISA (BD Biosciences, San Diego, USA).

In the assessment of cellular inflammation, bronchoalveolar lavage fluid (BALF) was obtained by cannulation of the trachea, and lavage with Hanks balanced salt solution (2×0.7 ml) (see Foster et al., 1996). BALF cell numbers were determined using a hemocytometer. Cells were cytocentrifuged and stained with May-Grunwald Giemsa. Differential cell counts were based on standard morphological characteristics of at least 250 cells/sample.

For the measurement of lung function, airways hyperresponsiveness was assessed by determination of airway resistance and dynamic compliance of the airways following challenge with aerosolised methacholine as previously described (Takeda et al., 1997). Anaesthetised, tracheostomised mice were mechanically ventilated (150 strokes/min, 0.18 ml tidal volume), aerosolised methacholine was administered (10 ul) in increasing concentrations (6.25 to 50 mg/ml), and lung function assessed.

Results are presented herein as mean±SEM. Lung function data were analysed by repeated measures one-way ANOVA by comparison of the entire dose-response curve. All other data were analysed by one-way ANOVA with Tukey's post-test.

Example 2

Effect of Vaccination Using *Streptococcus pneumoniae* Capsular Polysaccharide and Exotoxoid on the Development of Allergic Airways Diseases

*Streptococcus pneumoniae* (Type 3, strain NC012695; available under Accession Number ACTC6303 from the National Collection of Type Cultures, Egham, UK) was provided by Professor J. Kyd of the University of Can berra, Australia. Bacteria were cultured and prepared as described in Preston et al (2007). Briefly, prior to use, bacteria were stored at −80° C. in tryptone soya broth (TSB, Oxoid Australia) with 5% defibrinated horse blood, 0.5% glucose and 20% glycerol. Bacteria were freshly cultured before experiments on tryptone soy agar supplemented with 5% blood and 0.5% glucose and incubated for 16 hours (37° C., 5% $CO_2$). Colonies were harvested, and suspended in phosphate buffered saline (PBS). Ethanol-killed *Streptococcus pneumoniae* were prepared and stored at −80° C. until required.

Pneumolysoid was obtained from Professor James Paton of the University of Adelaide and was administered at a dose of 40 ng in PBS. Type 3 polysaccharide was obtained from the American Type Culture Collection and was administered at 2 mg per dose in PBS.

To assess the effect of immunisation with the capsular polysaccharide T3P and pneumolysoid (Ply), both individually and in combination, mice were immunized in three doses at 12 hour intervals on day 0, beginning at the time of OVA sensitization. Immunisation with T3P and Ply was compared with immunization using killed *Streptococcus pneumoniae* as described in co-pending International Patent Application No. PCT/AU2007/001098. As an allergic control, one group of mice was immunized with OVA, whilst as a non-allergic control, one group of mice was immunized with PBS. Each group comprised eight mice.

Figure 2:
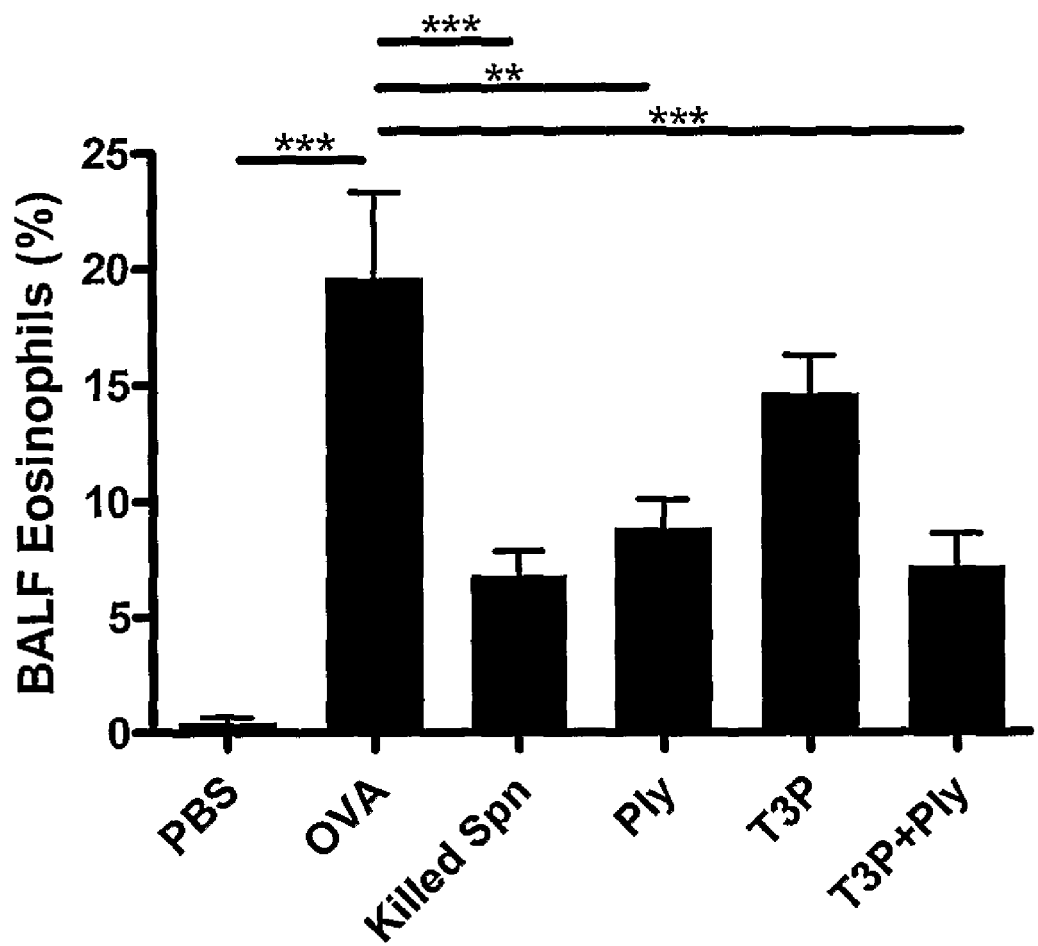
FIG. 2. BALF eosinophils in OVA-sensitised mice at day 16 following administration of phosphate buffered saline (PBS) (non-allergic control group), ovalbumin (OVA) (allergic control group), whole killed *Streptococcus pneumoniae* (killed Spn), pneumolysoid (Ply), type 3 polysaccharide (T3P), or type 3 polysaccharide with pneumolysoid (T3P+Ply). ( $p<0.01$, * $p<0.001$.) n=8 per group.

As shown in FIG. 2, there was a significant increase in eosinophils in the BALF of the allergic control group (OVA) compared to the non-allergic control group (PBS). Killed *Streptococcus pneumoniae*, Ply and T3P with Ply reduced the number of eosinophils significantly.

Figure 3:
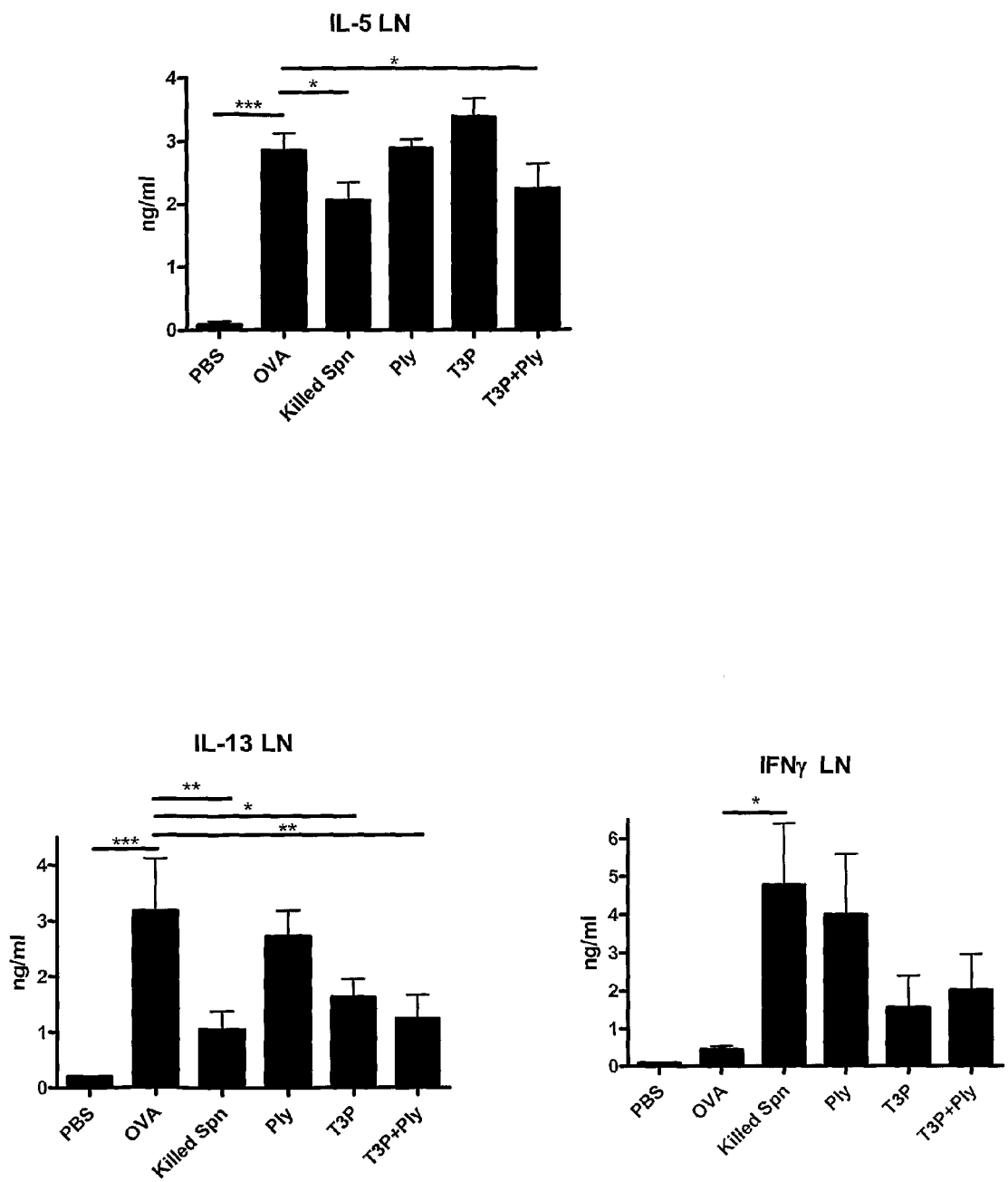
FIG. 3. IL-5 (A), IL-13 (B) and IFNγ (C) production from mediastinal lymph node T cells in OVA-sensitised mice at day 16 following administration of PBS, OVA, killed Spn, Ply, T3P, or T3P+Ply. (* $p<0.05$,  $p<0.01$, * $p<0.001$.) n=8 per group.
Figure 4A:
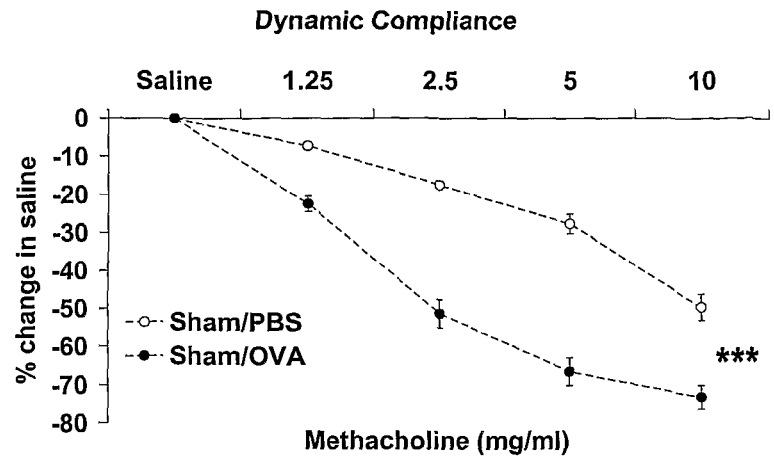
FIGS. 4A-4E. Airways hyperresponsiveness, as measured by dynamic compliance, in OVA-sensitised mice at day 16 following administration of PBS or OVA (A), killed Spn (B), Ply (C), T3P (D), or T3P+Ply (E). For (A), *** p<0.001 between PBS and OVA treatment. For (B) through (E), * p<0.05 and ** p<0.01 for the treatment group compared to allergic (OVA) controls. n=8 per group.
Figure 4B:
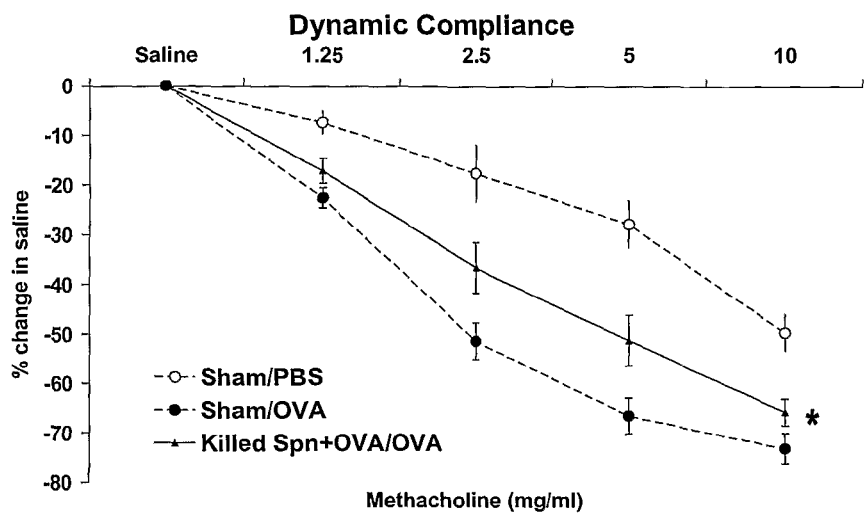
Figure 4C:
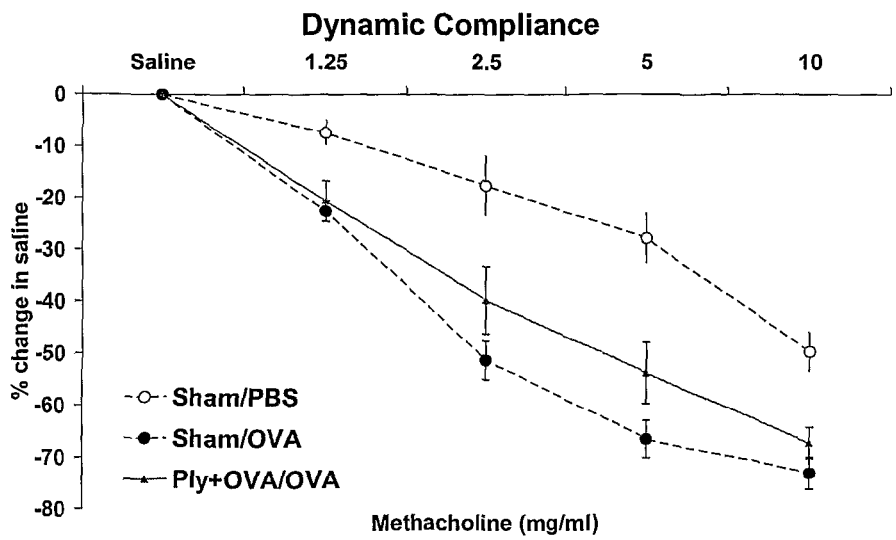
Figure 4D:
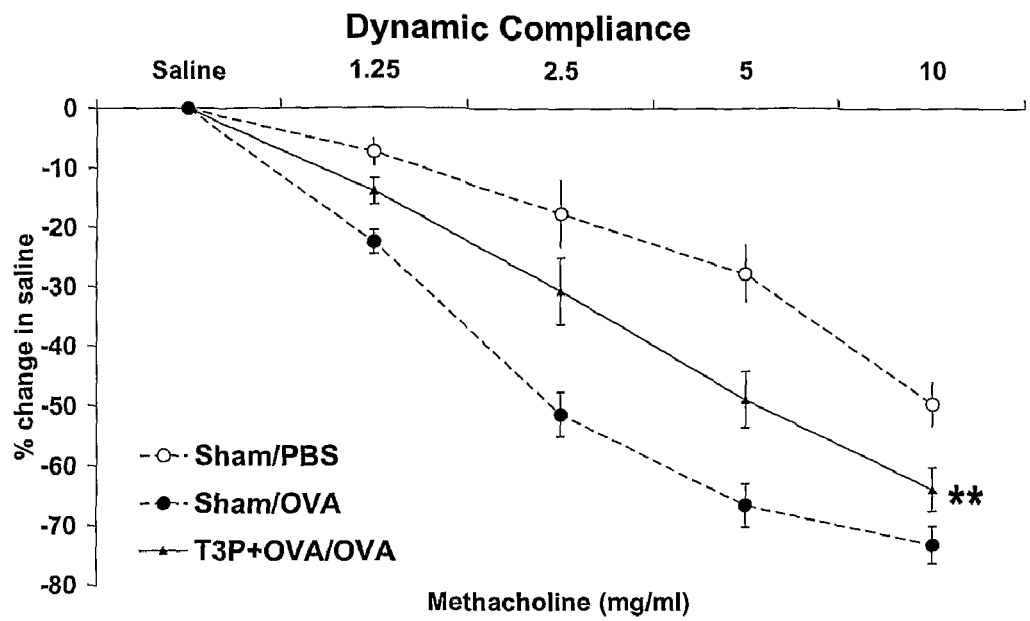
Figure 4E:
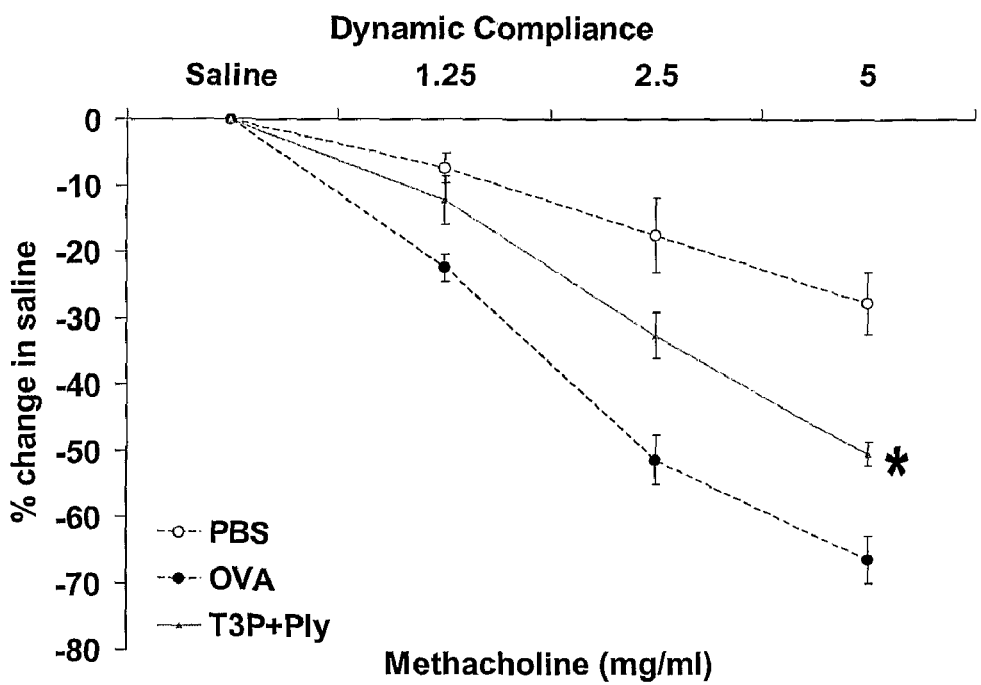
Figure 5A:
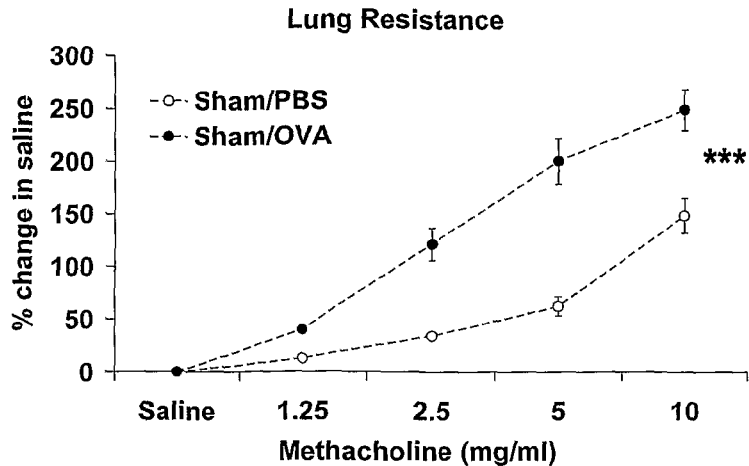
FIGS. 5A-5E. Airways hyperresponsiveness, as measured by lung resistance, in OVA-sensitised mice at day 16 following administration of PBS or OVA (A), killed Spn (B), Ply (C), T3P (D), or T3P+Ply (E). For (A), * p<0.001 between PBS and OVA treatment. For (B) through (E), p<0.05 and  p<0.01 for the treatment group compared to allergic (OVA) controls. n=8 per group.
Figure 5B:
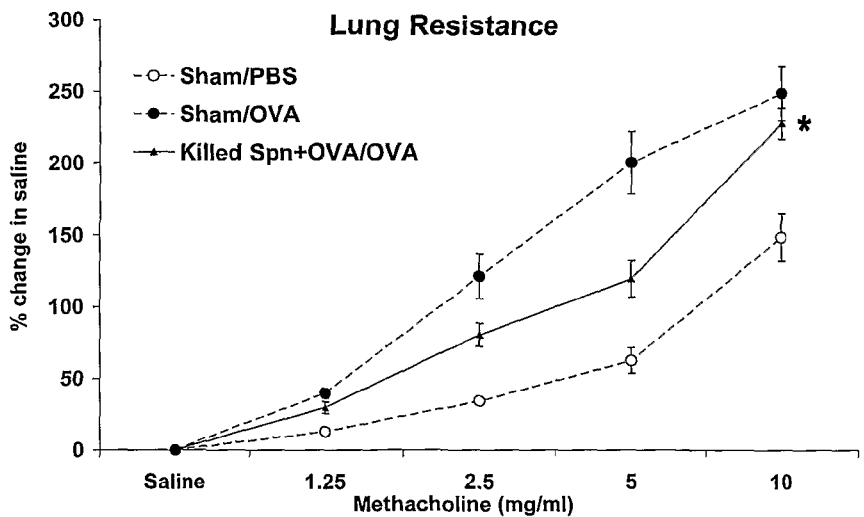
Figure 5C:
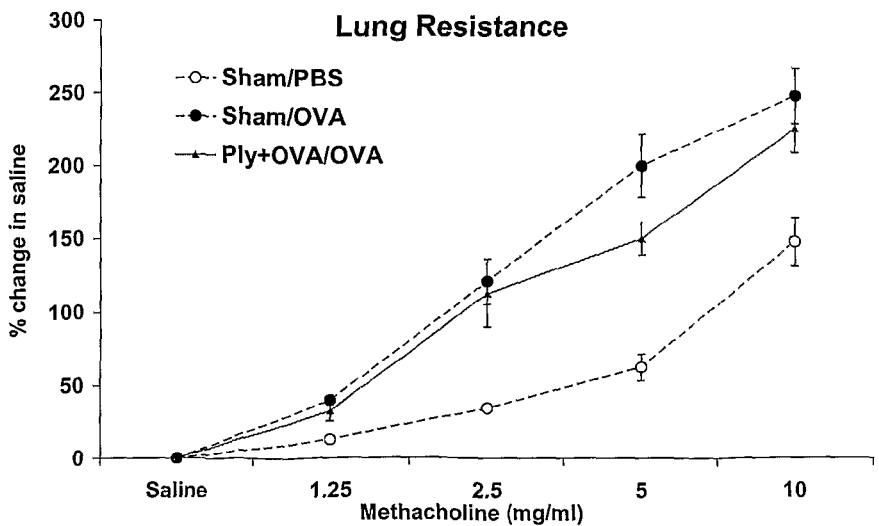
Figure 5D:
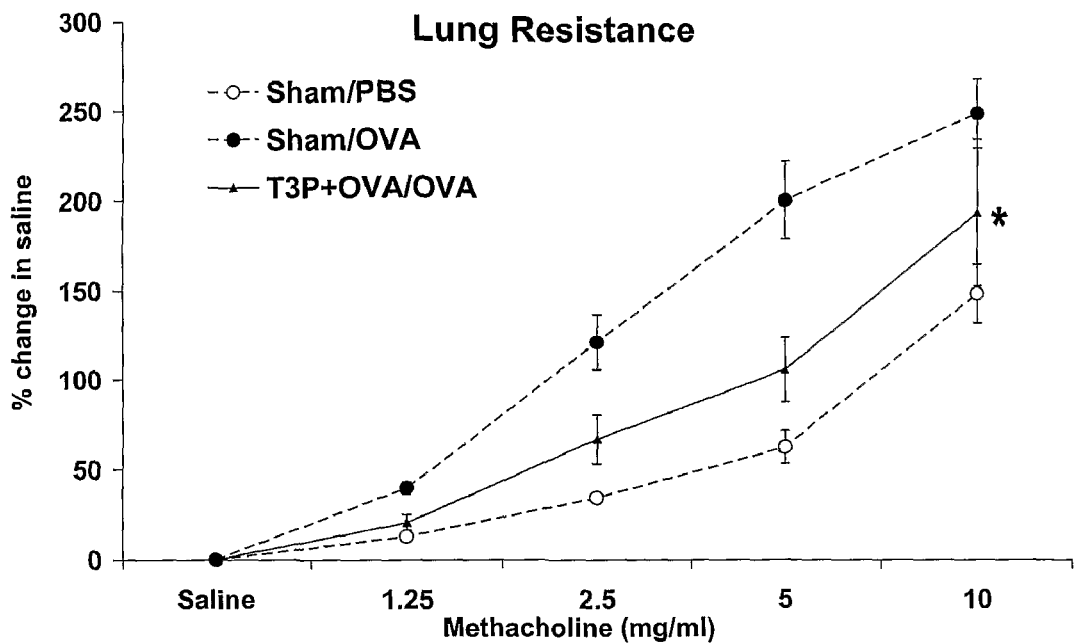
Figure 5E:
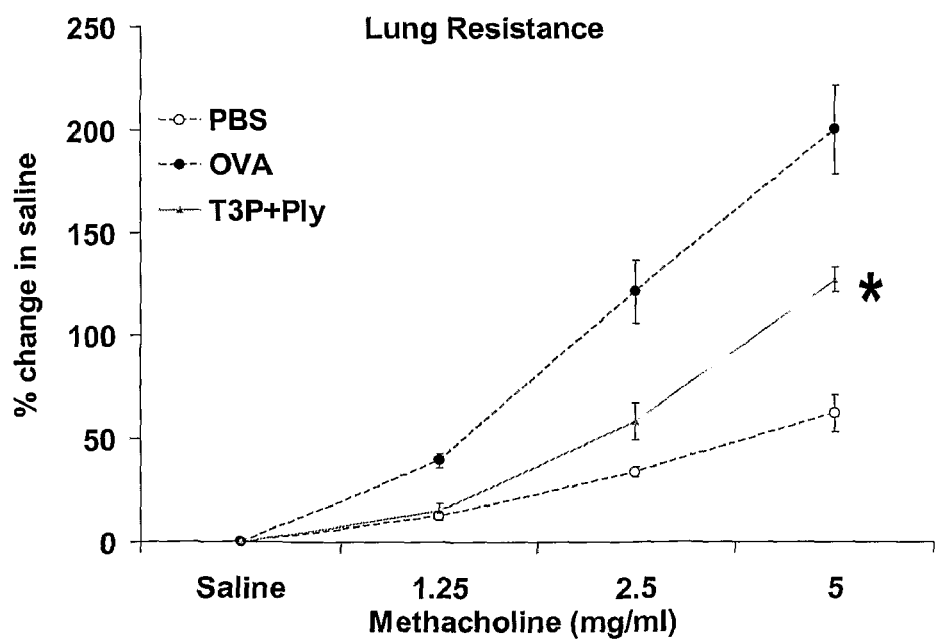

The inventors then determined the levels of production of the Th2 cytokines IL-5, IL-13 and IFNγ in mediastinal lymph nodes following immunizations as described above (see FIG. 3). IL-5 induces the development, maturation and mobilization of eosinophils into the lung. IL-13 induces recruitment of eosinophils to the lungs and is directly associated with airways hyperresponsiveness. IFNγ is a hallmark cytokine of Th1 cells. IFNγ also induces airways hyperresponsiveness and inflammation in the allergic lung. As shown in FIG. 3A, there was a significant increase in IL-5 in the allergic control group (OVA) compared to the non-allergic control group (PBS). IL-5 levels decreased when killed *Streptococcus pneumoniae* was administered and also when T3P+Ply were administered. Similar observations were made for IL-13 (FIG. 3B). When IFNγ was measured, importantly both killed *Streptococcus pneumoniae* and Ply induced an increase in IFNγ, however this was reduced when T3P+Ply were administered.

To assess the effect on airways hyperresponsiveness of immunisation with the caspsular polysaccharide T3P and the exotoxoid pneumolysoid (Ply), both individually and in combination, dynamic compliance and lung resistance (both indicators of the level of airways hyperresponsiveness) were measured (see FIGS. 4 and 5 respectively). Airways hyperresponsiveness results in a decrease in dynamic compliance as shown by the OVA (allergic control) group compared to the PBS (non-allergic control) group (FIG. 4A). Killed *Streptococcus pneumoniae* (FIG. 4B) and T3P (FIG. 4D) increased dynamic compliance, whilst Ply alone (FIG. 4C) had no effect. In contrast, T3P+Ply (FIG. 4E) significantly increased dynamic compliance thus effectively reducing airways hyperresponsiveness. Turning to lung resistance, as shown in FIG. 5A, airways hyperresponsiveness is associated with increased lung resistance as shown by the OVA group compared to the PBS group. Killed *Streptococcus pneumoniae* (FIG. 5B) and T3P (FIG. 5D) reduced lung resistance, whilst Ply alone (FIG. 5C) had no effect. In contrast, T3P+Ply (FIG. 5E) significantly reduced lung resistance thus effectively reducing airways hyperresponsiveness.

Example 3

Effect of Vaccination Using *Streptococcus pneumoniae* Capsular Polysaccharide, Exotoxoid, Cell Walls, CpG Oliguncleotides, and Combinations Thereof, on the Development of Allergic Airways Diseases The inventors have also investigated the effect of the addition of purified cell walls from unencapsulated *Streptococcus pneumoniae* and of bacterial CpG oligonucleotides on BALF eosinophil levels and Th2 cytokine (IL-5 and IL-13) production. Four components (T3P, Ply, purified cell walls (CW) and CpG oligonucleotides (CpG)) were administered, alone, in combination, and in all possible pairwise and triplet combinations. Experiments were conducted as described above in Example 2.

*Streptococcus pneumoniae* cell walls were purified as described (Tuomanen et al., 1985) with minor modifications. Briefly, unencapsulated *Streptococcus pneumoniae* R6 (ATCC BAA-255) was cultured overnight in Heart Infusion (HI) media to $5 \times 10^8$ cfu/ml. Following centrifugation and supernatant removal, bacteria were then ethanol killed (70% ethanol), resuspended in PBS and sonicated for 10 cycles. The suspension was then digested with 10 ug/ml DNase (Promega, Mannheim Germany) and 50 ug/ml RNase (Promega) for 1 hr at 37° C. followed by treatment with 100 ug/ml trypsin-EDTA with 10 mM CaCl for 2 hr at 37° C. The digest was sedimented by centrifugation (5200 rpm 20 min, 4° C.) and resuspended in SDS at 90° C. for 20 min, followed by 8 cycles of washing. The purified cell walls were resuspended in the initial volume and stored at −20° C. The equivalent of $2 \times 10^5$ cfu of cell wall preparation was administered per dose.

CpG oligonucleotides (Geneworks, SA) were of uniform length and of the following sequence:

5'-TCC ATG ACG TTC CTG ACG TT-3' (SEQ ID NO:1)

Figure 6:
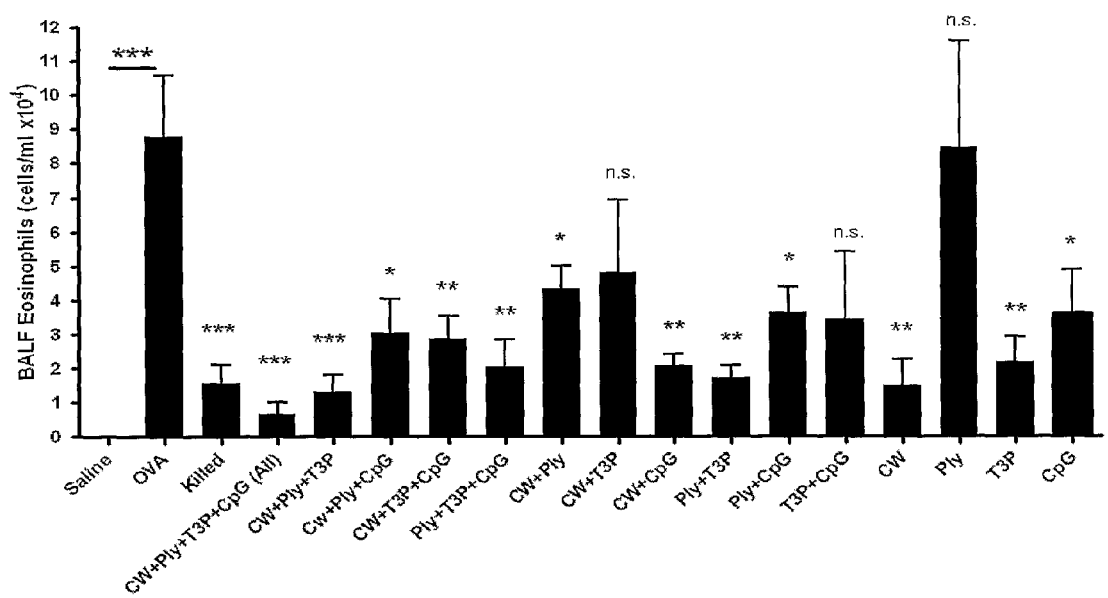
FIG. 6. BALF eosinophils in OVA-sensitised mice at day 16 following administration of PBS (saline), OVA, whole killed *Streptococcus pneumoniae* (killed), Ply, T3P, cell walls from unencapsulated *Streptococcus pneumoniae*, (CW), bacterial CpG oligonucleotides (CpG), and combinations of two or more of Ply, T3P, CW and CpG. *, p<0.001; , p<0.01; *, p<0.05; n.s., not significant. n=6-8 per group.
Figure 7A:
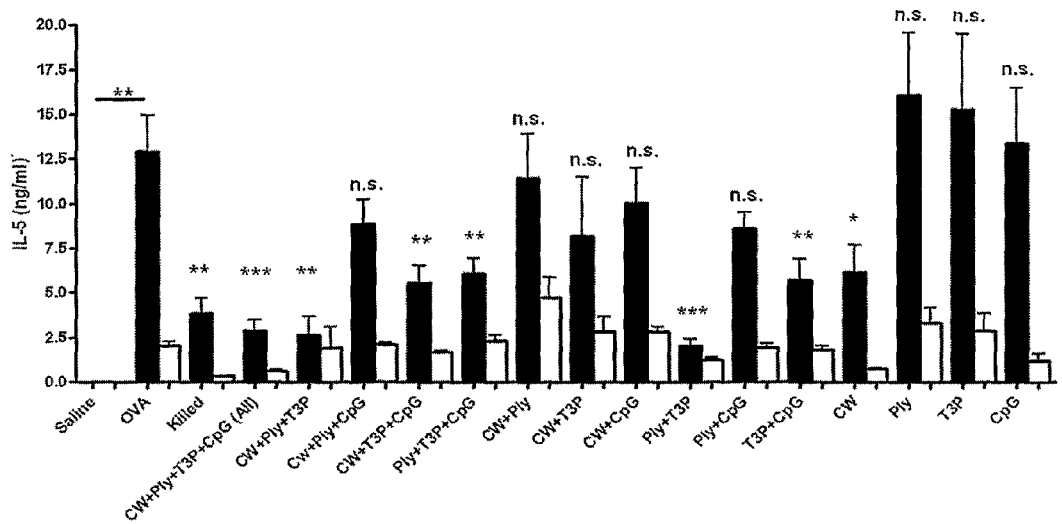
FIG. 7A-7B. IL-5 (A) and IL-13 (B) production from mediastinal lymph node T cells re-stimulated for 4-6 days with OVA in OVA-sensitised mice at day 16 following administration as described above for FIG. 6. *, p<0.001; , p<0.01; *, p<0.05; n.s.,not significant. Filled bars, stimulated cells; open bars, unstimulated cells. n=6-8 per group.
Figure 7B:
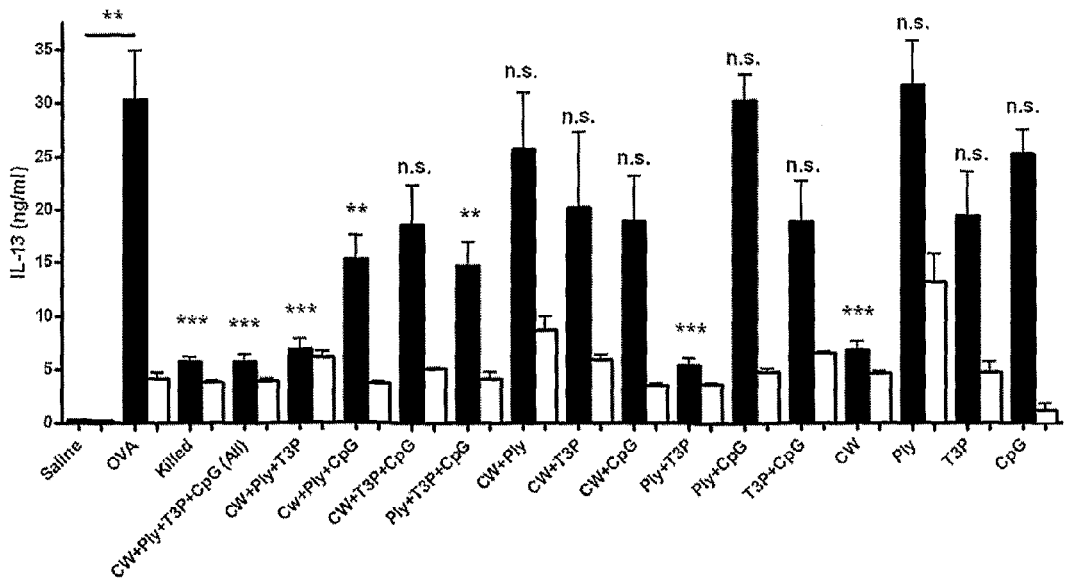
Figure 8A:
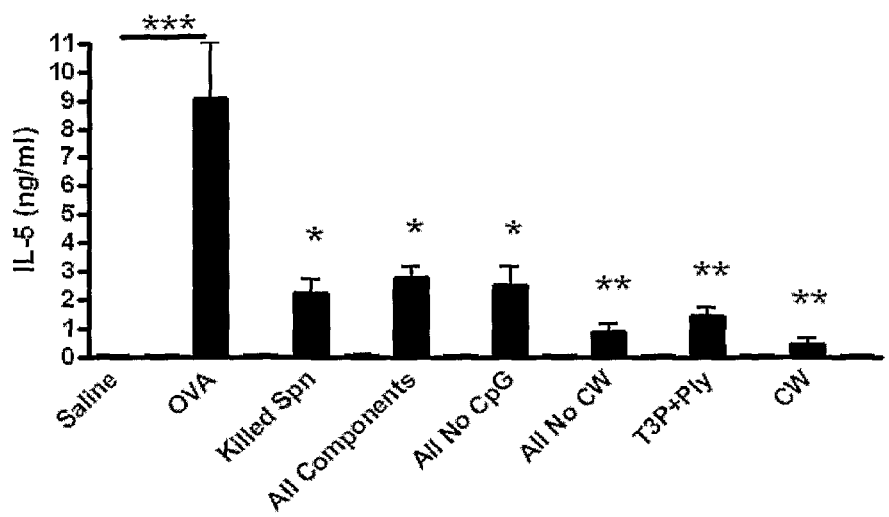
FIG. 8A-8B. IL-5 (A) and IL-13 (B) production from spleen lymphocytes re-stimulated for 4-6 days with OVA in OVA-sensitised mice at day 16 following administration of PBS (saline), OVA, killed Spn, Ply+T3P+CW+CpG (all components), Ply+T3P+CW (all no CpG), Ply+T3P+CpG (all no CW), T3P+Ply, and CW. *, p<0.001; , p<0.01; *, p<0.05; n.s., not significant. Filled bars, stimulated cells; open bars, unstimulated cells. n=6-8 per group.
Figure 8B:
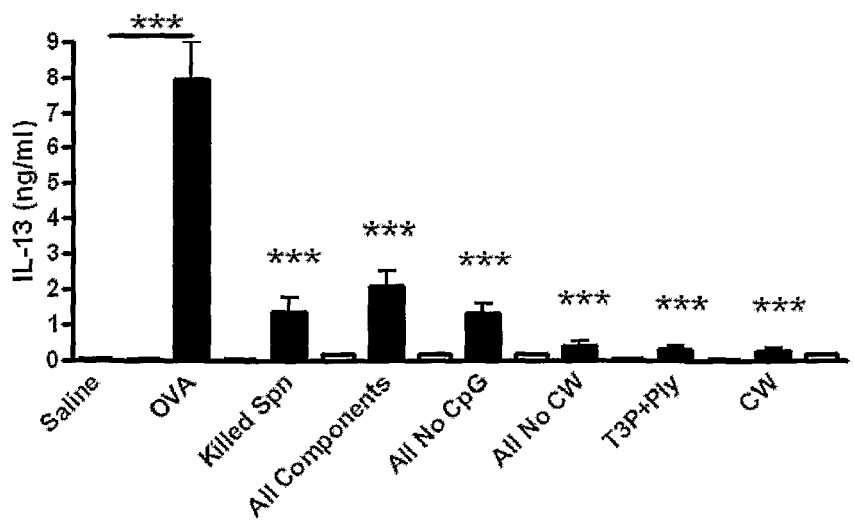

As shown in FIG. 6, the administration of both T3P+Ply+ cell walls and T3P+Ply+cell walls+CpG reduced the levels of BALF eosinophils ($p < 0.001$), to a greater degree than killed *Streptococcus pneumoniae*. These same combinations produced the greatest reduction in IL-5 levels from mediastinal lymph nodes (FIG. 7A), equivalent to Ply+T3P. Similar findings were found with IL-13 levels from mediastinal lymph nodes (FIG. 7B), Purified *Streptococcus pneumoniae* cell walls alone also produced a reduction in IL-13 levels consistent with that observed in the presence of Ply+T3P. Moreover, levels of both IL-5 and IL-13 from spleen lymphocytes were significantly reduced following administration of all individual and combinations thereof tested (see FIG. 8).

Figure 9A:
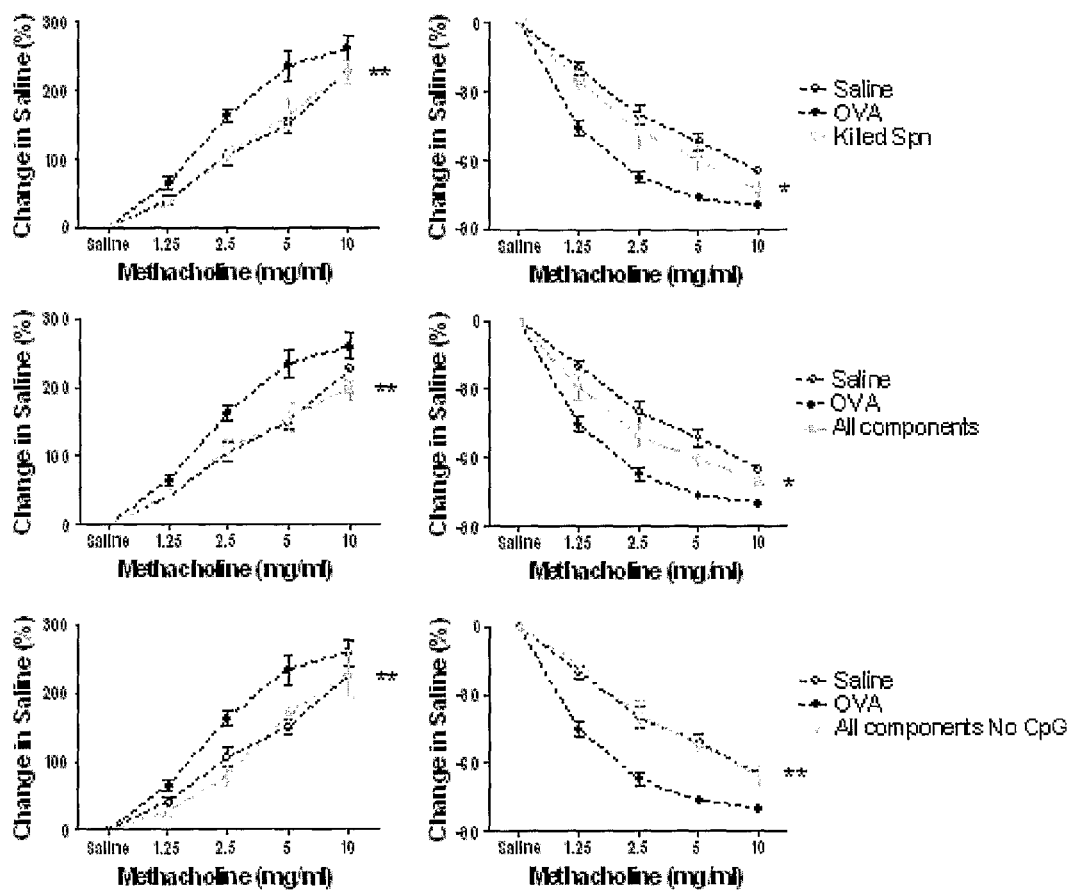
FIGS. 9A-9B. Changes in airways hyperresponsiveness, as measured by lung resistance (left hand graphs) and dynamic compliance (right hand graphs) in OVA-sensitised mice at day 16 following: (A) administration of PBS or OVA in comparison with killed Spn, Ply+T3P+CW+CpG (all), and Ply+T3P+CW (all no CpG); (B) administration of PBS or OVA in comparison with Ply+T3P+CpG (all no CW), T3P+Ply, and CW. n=6-8 per group. **, p<0.01; *, p<0.05.
Figure 9B:
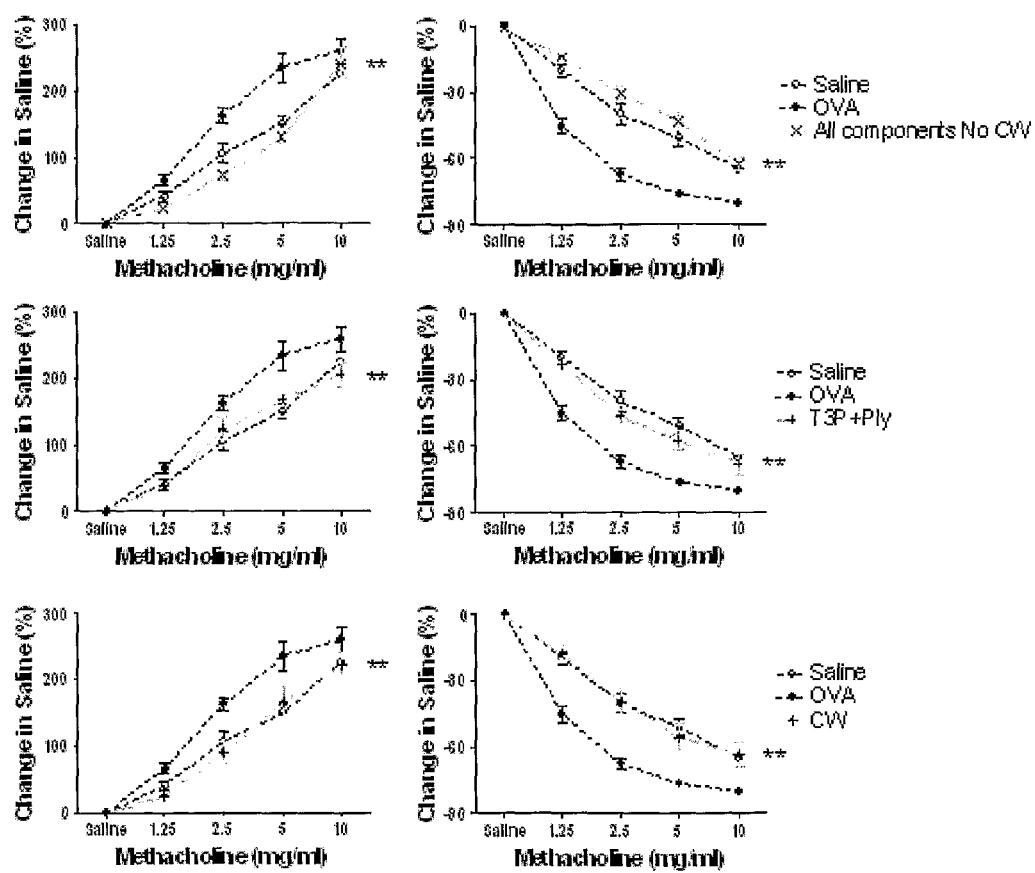
Figure 11A:
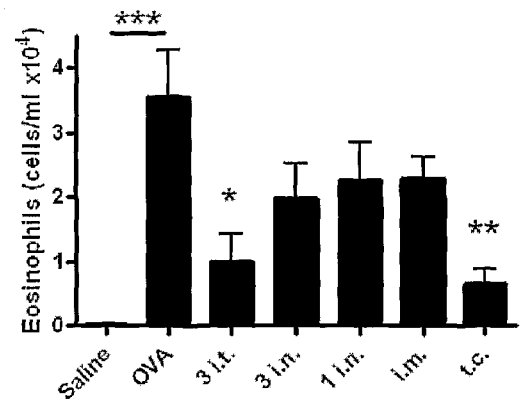
FIG. 11A-11D. Effect of route of administration of T3P+Ply on BALF eosinophils (A), production of IL-5 from mediastinal lymph node T cells (B), production of IL-5 from spleen lymphocytes (C) and production of IL-13 from spleen lymphocytes (D) in OVA-sensitised mice at day 16, when compared with saline and OVA administration. Routes of administration: intratracheal administration of three equivalent doses 12 hrs apart (3 i.t.); intranasal administration of three equivalent doses 12 hrs apart (3 i.n.); single intranasal administration (i.n.); single intramuscular administration (i.m.); and single transcutaneaous administration (t.c.). *, p<0.001; , p<0.01; *, p<0.05; n.s., not significant. n=6-8 per group.
Figure 11B:
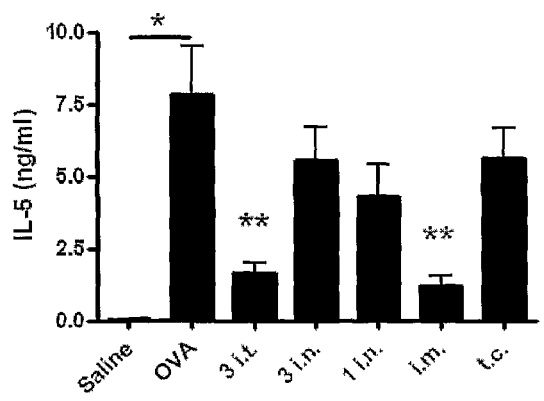
Figure 11C:
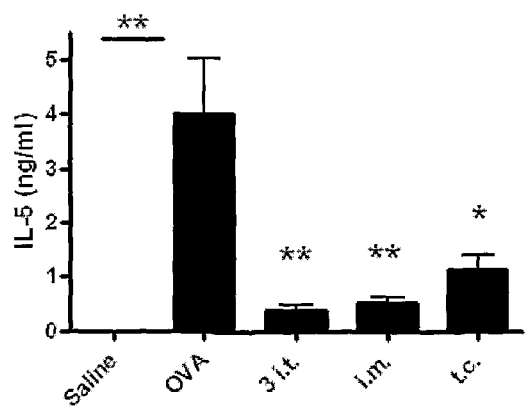
Figure 11D:
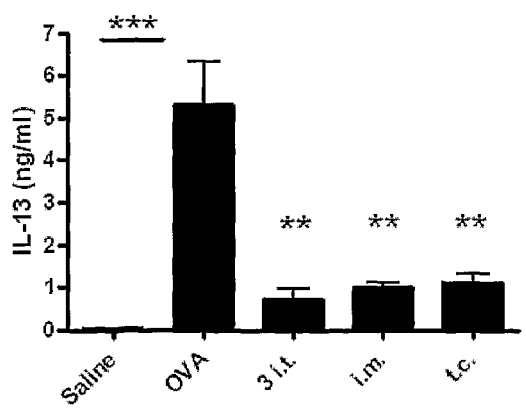

The effect of various combinations on hallmark features of airways hyperresponsiveness (dynamic compliance and lung resistance) were also tested, as described above in Example 2. As shown in FIG. 9, the following combinations T3P+Ply, T3P+Ply+cell walls, T3P+Ply+CpG and T3P+Ply+cell walls+CpG significantly increased dynamic compliance and reduced lung resistance. Purified *Streptococcus pneumoniae* cell walls alone produced similar changes.

tration (FIG. 11B), whereas intratracheal, intramuscular and transcutaneous administration all resulted in significant reductions in the levels of IL-5 and IL-13 from spleen lymphocytes (FIGS. 11C and 11D).

REFERENCES

Berry, L J et al. (2004) *Infect Immun* 72:1019-28
Carisen, K-H (2004) *Paediatric Respiratory Reviews* 5:45-51
Foster, P S et al. (1996) *J Exp Med* 183:195-201
Jones, P D et al. (2000) *Med Hypotheses* 55:40-2
Preston, J A et al. (2007) *Vaccine* 25:8154-62
Salisbury, D M, and N T Begg. (1996), Immunisation against infectious diseases, HMSO, London
Takeda, K et al. (1997) *J. Exp Med* 183:449-54
Talbot, T R et al. (2005) *N Engl J Med* 352:2082-90
Tuomanen et al. (1985) *J Infect Dis* 151:535-40

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial
<220> FEATURE:
<223> OTHER INFORMATION: Synthetic oligonucleotide sequence

<400> SEQUENCE: 1
tccatgacgt tcctgacgtt                                            20
```

Example 4

Effect of Ply+T3P Combination and Route of Administration Thereof on the Development of Allergic Airways Diseases To further investigate the potential of the Ply+T3P combination as an immunomodulatory therapy for allergic airways diseases, the inventors then determined the effects of Ply+T3P administered via four different routes of administration (intrtracheal, intranasal, intramuscular and transcutaneous). Dose levels and experimental procedures were as described above in Example 2. Between 6 and 8 mice were used in each test group. In the case of intratracheal administration, in order to provide a duration of maintenance of levels of antigens similar to that observed with *Streptococcus pneumoniae* infection, three equivalent doses of Ply+T3P were administered 12 hours apart. For intranasal administration, the effect of a single dose administration was compared to that of three equivalent doses 12 hours apart. For intramuscular and transcutaneous, single doses only were administered. For transcutaneous administration, a region of the back of each mouse was shaved and washed with acetone to remove any oil prior to administration of the Ply+T3P solution for absorption through the skin.

Figure 10:
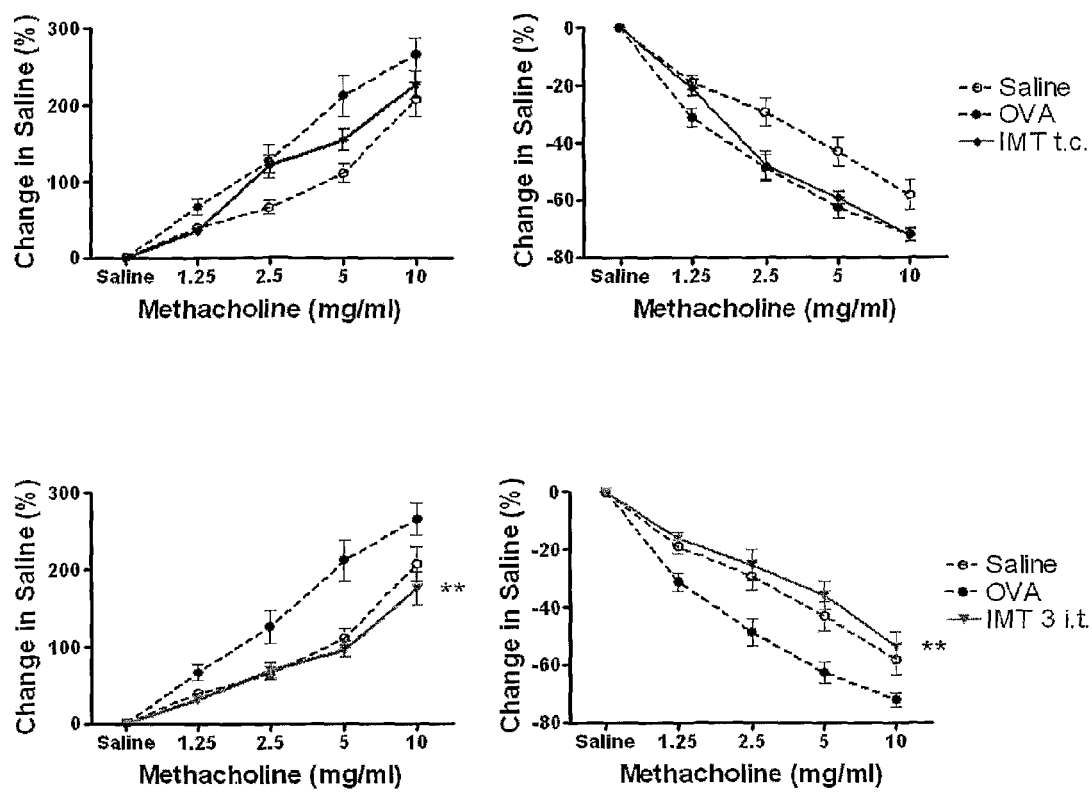
FIG. 10. Changes in airways hyperresponsiveness, as measured by lung resistance (left hand graphs) and dynamic compliance (right hand graphs) in OVA-sensitised mice at day 16 following immunomodulatory therapy (IMT) with T3P+Ply. Top row: single transcutaneaous administration (t.c.). Bottom row: intratracheal administration of three equivalent doses 12 hrs apart (3 i.t.). n=6-8 per group. **, p<0.01.

As shown in FIG. 10, a significant reduction (p<0.01) in airways hyperresponsiveness was observed for the group of mice administered Ply+T3P intratracheally with three equivalent doses 12 hours apart. This same treatment group, along with those in which administration was transcutaneous showed significantly reduced BALF eosinophil levels (FIG. 11A). Significant reductions in lymph node IL-5 levels were observed following intratracheal and intramuscular adminis-

The invention claimed is:

1. A method for the treatment or prevention of an allergic airways disease in a subject, the method comprising administering to the subject an effective amount of a *Streptococcus pneumoniae* capsular polysaccharide and a *Streptococcus pneumoniae* exotoxin or exotoxoid; wherein
    the capsular polysaccharide is the type 3 polysaccharide (T3P);
    the exotoxin or exotoxoid is pneumolysin or pneumolysoid (Ply); and
    the allergic airways disease is selected from asthma, asthma exacerbations, eosinophilic bronchitis, allergic rhinitis, chronic cough, sinusitis, angioedema, urticaria, chronic obstructive pulmonary disease, conjunctivitis and hay fever.

2. The method of claim 1 further comprising the administration of one or more additional antigenic or immunomodulatory constituents, components or fractions of *Streptococcus pneumoniae*, selected from purified cell walls, cell wall peptidoglycan, lipoteichoic acid, polysaccharides, protein, lipids, carbohydrates, glycoproteins, and fragments thereof.

3. The method of claim 2 wherein the additional constituent, component or fraction is purified *Streptococcus pneumoniae* cell wall.

4. The method of claim 3 wherein the purified cell wall is derived from an unencapsulated *Streptococcus pneumoniae* strain.

5. The method of claim 1 further comprising the administration of an immunopotentiator.

6. The method of claim 5 wherein the immunopotentiator comprises CpG oligonucleotides.

7. The method of claim 1 comprising the administration of T3P, Ply, purified cell wall from an unencapsulated *Streptococcus pneumoniae* strain and CpG oligonucleotides.

8. The method of claim 1 comprising the administration of T3P, Ply and purified cell wall from an unencapsulated *Streptococcus pneumoniae* strain.

9. The method of claim 1 comprising the administration of T3P, Ply and CpG oligonucleotides.

10. The method of claim 1 wherein the treatment or prevention prevents or suppresses the onset of an allergic airways disease, induces protective immunity against an allergic airways disease or suppresses an allergic immune response.

11. The method of claim 10 wherein the allergic immune response is associated with eosinophilia, mucous secreting cell expression, airway hyperresponsiveness and/or any Th2-mediated immune response.

* * * * *